United States Patent [19]

Van Dijk et al.

[11] 4,196,216

[45] Apr. 1, 1980

[54] NOVEL BENZYLIDENE AMINI-OXYALKYL CARBOXYLIC ACIDS AND CARBOXYLIC ACID DERIVATIVES

[75] Inventors: Jan Van Dijk; Volkert Claassen; Johannes M. A. Zwagemakers, all of Weesp, Netherlands

[73] Assignee: U.S. Philips Corporation, New York, N.Y.

[21] Appl. No.: 847,765

[22] Filed: Nov. 2, 1977

Related U.S. Application Data

[60] Division of Ser. No. 751,489, Dec. 17, 1976, Pat. No. 4,071,686, which is a continuation of Ser. No. 286,874, Sep. 7, 1972, abandoned, which is a continuation of Ser. No. 885,628, Dec. 16, 1969, abandoned.

[30] Foreign Application Priority Data

Dec. 17, 1968 [NL] Netherlands ............................ 6818074

[51] Int. Cl.$^2$ .................... A61K 31/24; A61K 31/165; A61K 31/15; C07C 103/75
[52] U.S. Cl. ..................................... 424/309; 424/319; 424/320; 424/327; 260/559 H
[58] Field of Search ...................... 560/35; 260/501.11, 260/501.17, 559 A, 429.9, 519, 559 H; 424/309, 316, 319, 320, 327

[56] References Cited

U.S. PATENT DOCUMENTS 4,071,686  1/1978  Van Dijk et al. ...................... 560/35

FOREIGN PATENT DOCUMENTS 42-16296  9/1967  Japan ........................................ 260/519
42-21334 10/1967  Japan ........................................ 260/519

OTHER PUBLICATIONS

Vecchio, Chem. Abstracts, vol. 54, col. 5524(c)–5524(d), 1960.

*Primary Examiner*—Joseph E. Evans
*Assistant Examiner*—G. T. Breitenstein
*Attorney, Agent, or Firm*—Norman N. Spain

[57] ABSTRACT

Certain nuclear substituted benzylidene amino oxyalkyl carboxylic acids esters, amides and salts thereof have been found to have a strong anti-inflammatory activity and a potent analgetic activity. In addition, some of the compounds have an activity against Rhino virus. An example is [(4-chlorobenzylideneamino)oxy] acetic acid.

11 Claims, No Drawings

NOVEL BENZYLIDENE AMINI-OXYALKYL CARBOXYLIC ACIDS AND CARBOXYLIC ACID DERIVATIVES

This is a division of application Ser. No. 751,489, filed Dec. 17, 1976, and now U.S. Pat. No. 4,071,686 said application Ser. No. 751,489 in turn being a continuation of application Ser. No. 286,874, filed Sept. 7, 1972 and now abandoned and said application Ser. No. 286,874 being in turn a continuation of application Ser. No. 885,628, filed Dec. 16, 1969 and now abandoned.

The invention in this case relates to novel benzylidine amino oxyalkyl carboxylic acids and derivatives thereof having antiinflammatory and analgetic activities.

Some compounds are known for treating rheumatic afflictions and similar types of illnesses. However, the known compounds have been found to be of little value because of the existance of undesirable side effects or a high toxicity level. Thus the compound (N-p.chlorophenyl-5-methoxy indolyl-3) acetic acid, while being highly potent is of little use in the treatment of rheumatic illnesses because it has a high toxicity level thus making its therapeutic level quite low.

According to the invention, a new and novel group of benzylideneamino oxyalkyl carboxylic acids and derivatives have been prepared. These novel compounds have the following general structure:

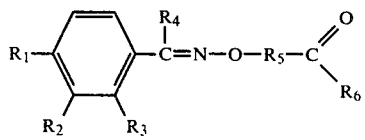

wherein $R_1$ is halogen (fluorine, chlorine, bromine or iodine), $CF_3$, $CH_3SO_2CH_3$, $SO_2NH_2$ or hydrogen, $R_2$ is halogen (fluorine, chlorine bromine or iodine) or hydrogen when $R_1$ is other than hydrogen, $R_3$ is hydrogen or when $R_2$ is hydrogen halogen (fluorine, chlorine, bromine and iodine), $R_4$ is hydrogen or methyl, $R_5$ is alkylene of up to 3 carbon atoms, $R_6$ is OH, alkoxy of up to 8 carbon atoms, —NH—$NH_2$,—$NH_2$, mono- or dialkylamino in which each alkyl group contains up to 3 carbon atoms, benzyloxy or the radical $OR_7$ wherein $R_7$ is a metal atom such as Na, Ca, Mg, Zn or K, ammonium, hydroxy ethyl dimethyl ammonium or hydroxyethyl diethyl ammonium.

It has been found that these novel compounds of the invention are useful in that they generally have strong anti-inflammatory activities along with strong analgetic activities accompanied by only a very low level of toxicity.

This low level of toxicity appears from the following table:

| compound of foregoing formula wherein | | | | | | $LD_{50}^{24}$ | $LD_{50}^{48}$ | route of |
|---|---|---|---|---|---|---|---|---|
| $R_1$ | $R_2$ | $R_3$ | $R_4$ | $R_5$ | $R_6$ | mg/kg | mg/kg | administration |
| Cl | H | H | H | $CH_2$ | OH | >320 | | par(enteral) |
| Cl | Cl | H | $CH_3$ | $CH_2$ | OH | >320 | | par. |
| Cl | H | H | $CH_3$ | $CH_2$ | OH | >1000 | >1000 | or(al) |
| Cl | H | H | $CH_3$ | $(CH_2)_2$ | OH | >100 | | par. |
| Cl | H | H | $CH_3$ | $CH_2$ | $NH_2$ | >1000 | >1000 | or |
| Cl | H | H | $CH_3$ | $CH_2$ | $OCH_3$ | >1000 | >1000 | or |
| Cl | H | H | $CH_3$ | $CH_2$ | $NHCH_3$ | >1000 | | or |
| Cl | H | H | $CH_3$ | $CH_2$ | $(CH_3)_2N$ | >1000 | | or |
| Cl | Cl | H | $CH_3$ | $CH_2$ | $NH_2$ | ≈1000 | | or |
| Cl | H | H | $CH_3$ | $(CH_2)_2$ | $NH_2$ | >1000 | | or |
| Cl | H | H | $CH_3$ | $(CH_2)_3$ | OH | >320 | | par. |
| Cl | H | H | $CH_3$ | $CH_2$ | $OCH(CH_3)_2$ | >1000 | | or |
| H | Cl | H | $CH_3$ | $CH_2$ | OH | >320 | | par. |
| Br | H | H | $CH_3$ | $CH_2$ | OH | >100 | | par. |
| $CH_3$ | H | H | $CH_3$ | $CH_2$ | OH | >320 | | par. |
| $CH_3SO_2$ | H | H | $CH_3$ | $CH_2$ | OH | >320 | | par. |
| Cl | H | H | $CH_3$ | $CH_2$ | $OnC_8H_{17}$ | >1000 | | or |
| Cl | H | H | $CH_3$ | $CH_2$ | $OCH_2C_6H_5$ | >1000 | | or |
| Cl | H | Cl | $CH_3$ | $CH_2$ | OH | >320 | | par. |
| Cl | H | H | $CH_3$ | $CH_2$ | $NHNH_2$ | ≈1000 | | or |

It has been found that compounds of the following formula are particularly useful because of their very strong activities:

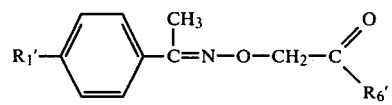

wherein $R'_1$ is bromine or chlorine, and $R'_6$ is $NH_2$, OH, alkoxy or up to 3 carbon atoms or the radical $OR_7$ where $R_7$ has the meaning as previously given. Of these compounds [α-methyl-4-chlorobenzylideneamino) oxy] acetic acid and its salts, [α-methyl4-chlorobenzylideneamino)oxy] acetic acid methyl ester and [α-methyl-4-chlorobenzylideneamino)oxy] acetamide have particularly strong activities.

Due to their anti-inflammatory and analgetic effects, the compounds of the invention may be useful in the treatment of such illnesses as rheumatoid arthritis, Bechterew's disease, arthritis psoriatica, osteoarthrosis, acute gout, periarthritis humeroscapularis, acute sterile non-infected bursitis, thrombophlebitis and acute polyarthritis rheumatica.

The compounds of the invention may be orally, rectally or parenterally administered with dosages depending upon the severity and type of disease. In any case, the physician will have no difficulty in determining the proper dosage to use. Generally, 50 to 1000 mg are administered daily divided, if required, into several portions. Usually from 100 to 500 mg daily will suffice.

As substances with which the compounds can be formulated may be mentioned; glucose, cellulose, starch, maize starch, pectine, agar, magnesium stearate and other stearates, talc, carboxymethylcellulose sodium, ethylene diamino tetra acetic acid (E.D.T.A.), ascorbic acid, ultra amylopectine, SiO$_2$ derivatives, sodiumstearylfumarate, alginates, water, n.propylene glycol, glycerine, ethanol, sodiummetabisulphite, benzylalcohol, phenol and substituted phenols, sodium citrates, -borates and -tartrates, carbowaxes, saturates and unsaturated fats, methyl-p.hydroxy benzoate, n.propyl-p.hydroxybenzoate.

The anti-inflammatory activity of the compounds was determined in the carageenin test carried out according to a modification of the method of Winter, Risley and Nuss, Proc. Soc. Exp. Biol. 111-544-(1962).

In this test, the reduction of the swelling produced by the carageenin serves as a measure of the anti-inflammatory effect.

The test was performed with male rats of weight about 220 g. The animals are made to fast for the 16 hours preceding the test. The substances to be tested are suspended in a 1% tragacanth solution and aministered orally. Immediately after the administration of the substance, a water loading of up to 5 ml per animal is performed. 1 hour thereafter, 0.05 ml of 1.5% carrageenin solution is intraplantarly injected and the thickness of the foot (dorsal plantar distance) is determined by means of a special micrometer.

3 hours after the administration of the carageenin the thickness of the oedema is determined. The swelling of the foot is expressed in a percentage relative to the zero hour value. The inhibition percentage is calculated according to the relation:

$$\frac{\text{percentage of blanko group} - \text{percentage of test group}}{\text{percentage of blank group}} \times 100$$

From the results of a series of dosages an ED$_{50}$ value was computed. This is the dosage which gives a reduction of 50% relative to the blank group.

The analgetic activity of the compounds was determined by a modification of the method of Randall and Sellito (Arch. Int. Pharmacodyn. 109 409 (1957)).

The reduction of the pain response due to increasing pressure on a yeast-inflamed rat foot is used as a criterion for the analgetic activity.

The test is performed with male rats, weight from 100 to 150 g. One hour before the administration of the test preparation the animals are given an intraplantar injection of 0.1 ml of 20% yeast suspension. The compounds to be tested are suspended in a 1% tragacanth solution and administered orally. One hour, two hours and four hours after the administration of the test substance the pain threshold value is measured with increasing pressure on the inflamed foot.

As a comparison, the pain reaction of a group of animals not treated, with a pharmacon was determined. The results are expressed as a percentage of the mean blank value.

From the results of a series of dosages an ED$_{50}$ value, i.e. the dosage which produces a 100% increase of the pain threshold, was calculated.

As compounds having an interesting activity against. Rhine virus we may mention:

[(α-methyl-4-chlorobenzylidene amino)oxy] acetamide,

[(α-methyl-3,4-dichlorobenzylidene amino)oxy] acetamide,

N-n.butyl-[(α-methyl-4-chlorobenzylidene amino)oxy] acetamide,

[(α-methyl-4-chlorobenzylidene amino)oxy] acethydraxide,

[(α-methyl-2,4-dichlorobenzylidene amino)oxy] acetic acid,

4-[(α-methyl-4-chlorobenzylidene amino)oxy] butyric acid.

The compounds according to the invention can be prepared by known methods.

Accordingly, the invention relates also to a method of producing novel benzylidene amino oxyalkyl carboxylic acids and carboxylic acid derivatives which is characterized in that compounds of the general formula

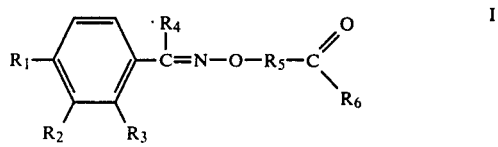

where
R$_1$ is a halogen, CF$_3$, CH$_3$, SO$_2$CH$_3$ or SO$_2$NH$_2$,
R$_2$ is a halogen or CH$_3$, whilst either R$_1$ or R$_2$ may be hydrogen.
R$_3$ is hydrogen or, if R$_2$ is hydrogen, a halogen,
R$_4$ is hydrogen or CH$_3$,
R$_5$ is a possibly branched alkylene group containing up to 3 carbon atoms,
R$_6$ is OH, an alkoxy containing up to 8 carbon atoms, benzyl oxy, NH–NH$_2$, NH$_2$, a mono- or dialkyl amino, in which the or each alkyl group contains up to 3 carbon atoms, or the radical OR$_7$, where
R$_7$ represents a metal atom, an ammonium group, a hydroxy-ethyldimethyl ammonium group or a hydroxyethyldiethyl ammonium group, are prepared by methods which are known for preparing compounds of this type and by similar methods.

The compounds according to the invention may, for example, be obtained by reacting a compound of the formula

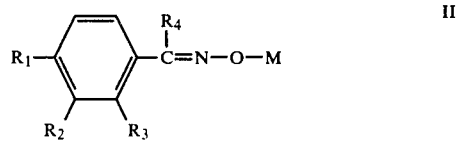

with a compound of the formula

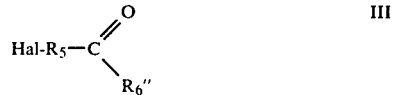

in which formulas R$_1$ to R$_5$ have the same meanings as in the formula I, M is a metal atom, for example Na or K, Hal is a halogen atom, for example chlorine or bromine, and R$_6''$ is OH, NHNH$_2$, NH$_2$, a mono- or dialkylamino in which the or each alkyl group contains up to 3 carbon atoms, an alkoxy containing up to 8 carbon atoms or a benzyloxy. The reaction is preferably carried out in a polar solvent, such as dimethylformamide, dimethylsulfoxide, alcohols and the like at temperatures between room temperature and the boiling point of the reaction mixture and in the presence of an acid binder, for example an ethanolate. Acids of the formula I obtained in this reaction can subsequently be converted into the salts of the formula I (R$_6$=OR$_7$).

The compounds according to the invention may alternatively be prepared by reacting a compound of the general formula:

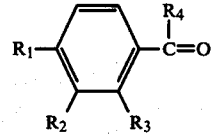   IV with a compound of the general formula:

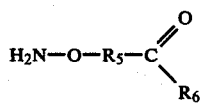   V in which formula the symbols have the same meanings as in the formula I. This reaction also preferably is carried out in a polar inert solvent, for example one of the aforementioned solvents. The reaction temperatures as a rule lies between room temperature and the boiling point of the solvent.

The acids of the formula VI

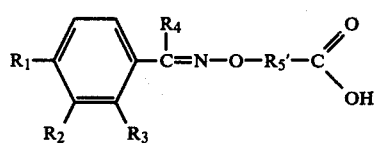   VI and their salts, in which formula $R_1$ to $R_4$ have the same meanings as in the formula I and $R_5'$ is a propylene or a possibly branched ethylene group, can be prepared by reacting a compound of the formula II

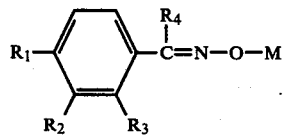   II with a compound of the formula

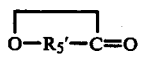   VII

The reaction is preferably performed in an inert solvent, such as, for example, N-Methyl-2-pyrrolidon, benzene or the like, at temperatures between room temperature and the boiling point of the solvent.

The compounds of the formula

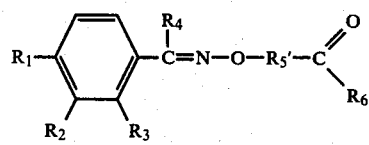   VIII where $R_1$ to $R_4$ and $R_6$ have the same meanings as in the formula I and $R_5'$ is a propylene or possibly branched ethylene group, can be obtained by reacting a compound of the formula

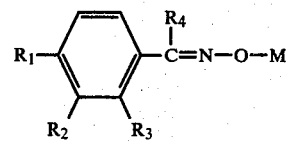   II with a compound of the formula

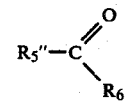   IX where $R_5''$ is an ethenyl group or a propenyl-1,-2 or -3 group. The reaction is preferably carried out in an inert solvent, for example in an alcohol, for example ethanol. The reaction temperature as a rule lies between 0° C. and the boiling point of the reaction mixture.

The compounds of the formula

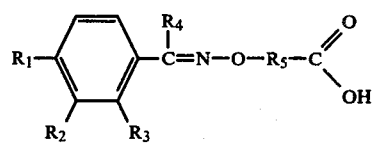   X and their salts—$R_1$ to $R_5$ have the same meanings as in the formula I—may also be obtained by saponifying a nitrile of the formula

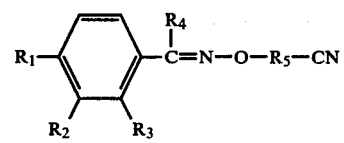   XI where $R_1$ to $R_5$ have the same meanings as in the formula I, with a base. The reaction is preferably carried out in an inert solvent, such as an alcohol, at a temperature not higher than the boiling point of the reaction mixture.

Esters of the formula

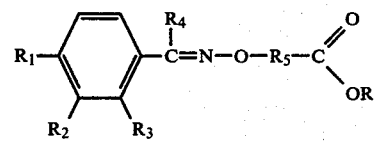   XII may also be obtained by reacting a nitrile of formula XI with an alcohol ROH in the presence of an acid, and decomposing the reaction product with water. In these formulas $R_1$ to $R_5$ have the same meanings as in the formula I. R represents an alkyl group containing up to 8 carbon atoms or a benzyl group. The reaction is preferably carried out in an inert solvent, for example an ether, such as diisopropyl ether. The reaction temperature lies between 0° C. and 40° C.

Acids of the formula I can be converted into the corresponding esters of the formula I by means of alcohols, as the case may be by way of the acid chlorides. Esters of the formula I can be converted into amides or hydrazides of the formula I by means of ammonia or a mono- or dialkyl amine, or hydrazine, respectively. The acids of the formula I can be obtained from amides and esters of the formula I by saponification.

The compounds according to the invention can be converted into pharmaceutical preparations, such as, for example, tablets, pills, powders, injection liquids, salves, suppositories dragees and the like, by known methods. Hence the invention also relates to the production of pharmaceutical preparations and to the preparations themselves.

Suitable carrier materials are the substances commonly used for this purpose in pharmacy.

The invention will now be described more fully with reference to the following examples.

(1) [(4-chlorobenzylidene amino)oxy] acetic acid.

4.2 g of 4-chlorobenzaldehyde and 3.3 g of hemihydrochloride of amino-oxyacetic acid were dissolved in 50 ml of 90% ethanol. The solution was mixed with 7.4 g of sodium acetate and then refluxed for 20 minutes. The reaction mixture was subsequently concentrated by evaporation in a vacuum. After an excess of 2 N sodium hydroxide had been added, the residue was twice extracted with ether, after which the remaining aqueous solution was acidified with 2 N hydrochloric acid and again extracted twice with ether. The latter ethereal solution was washed twice with water, then dried over anhydrous sodium sulfate and subsequently concentrated by evaporation. The residue was crystallized from a mixture of ether and petroleum ether, them from highly dilute ethanol and ultimately twice from a mixture of benzene and petroleum ether. The substance obtained melted at 121° C.–123° C.

(2) [(α-methyl-3,4-dichlorobenzylene amino)oxy] acetic acid.

In the manner described in example 1, the above substance was obtained by boiling 4.73 g or 3,4-dichloroacetophenone, 2.74 g of hemihydrochloride or aminooxyacetic acid and 6.15 g of sodium acetate in 80% ethanol for one hour. After one crystallisation from a mixture of benzene and petroleum ether, the melting point was 128° C.–129° C.

(3) [(α-methyl-4-chlorobenzylidene amino)oxy] acetic acid.

15.7 g of 4'-chloroacetophenone oxime was added to a solution of 2.13 g of sodium in 80 ml of absolute ethanol. The solvent was distilled off as far as possible from the solution in a vacuum. The residue was mixed with 33 g of α-chloroacetic acid ethyl ester and then refluxed for half an hour. Subsequently, the excess of α-chloroacetic ester was removed at 80° C. in a vacuum. The residue contained the ethyl ester of [(α-methyl-4-chlorobenzylidene amino)oxy] acetic acid. This ester was saponified by boiling it with 55 ml of 2 N sodium hydroxide for 1 hour. The reaction mixture was cooled and then extracted 5 times with ether. The extracted alkaline solution was acidified with 100 ml of 2 N hydrochloric acid and then extracted twice with ether. The latter ethereal extracts were washed 4 times with water,~ after which the ether was distilled off. The solid residue was crystallized once from a mixture of benzene and petroleum ether and then purified by washing a solution of the residue in a caustic soda solution with ether and reacidifying it. After another crystallisation from a mixture of benzene and petroleum ether the pure substance was obtained. Melting point 115.5° C. to 116.5° C.

(4) 2-[(α-methyl-4-chlorobenzylidene amino)oxy] propionic acid.

To a solution of 1.85 g of a sodium in 150 ml of absolute ethanol 6.8 g of 4-chloroacetophenone oxime and 8.6 g of α-bromopropionic acid were added in this order with stirring. After the mixture had been stirred for 1 hour the ethanol was removed in a vacuum. The residue was mixed with water and the mixture was washed twice with ether. The aqueous solution then was acidified and extracted twice with ether. The ethereal extracts were washed 6 times with water, dried over anhydrous sodiumsulfate and concentrated by evaporation. After crystallisation of the residue from petroleum ether, the superscribed substance was obtained. After it had been washed once with water and crystallized from a mixture of benzene and petroleum ether te melting point was 88° C.–89° C.

(5) [(α-methyl-4-chlorobenzylidene amino)oxy]acetamide.

A solution of 2.9 g of sodium in 75 ml of absolute ethanol was mixed with 21.4 g of 4'-chloroacetophenone oxime and then concentrated by evaporation in a vacuum to a constant weight. The residue was mixed with 75 ml of dimethyl formamide and 11.8 g of α-chloroacetamide. The temperature was maintained below 40° C. by cooling. The mixture was stirred overnight at room temperature, after which the solvent was removed in a vacuum. The residue was dissolved in ether and water. The ethereal solution was washed twice with sodium hydroxide and thrice with water. The solution was mixed with a small amount of chloroform, treated once with activated carbon and a filter acid (hyflo), whereupon after some concentration by evaporation and after the addition of petroleum ether the superscribed substance crystallized out. It was recrystallized from a mixture of chloroform, ether and petroleum ether. Melting point 103° C.–104° C.

(6) [(α-emthyl-4-chlorobenzylidene amino)oxy] acetic acid methyl ester.

A solution of 17.0 g of the [(α-methyl-4-chlorobenzylidene amino)oxy] acetic acid obtained by a method as described in one of the preceding examples in 60 ml of methanol, to which 1 ml of concentrated sulfuric acid had been added, was refluxed for 8 hours. The larger part of the methanol was then distilled off in a vacuum and the residue was washed with ether. This ethereal solution was washed once with water and 4 times with portions of 20 ml of 2 N sodium hydroxide each. The solution was dried over anhydrous sodium sulfate and the solvent was distilled off. After distillation in a vacuum the residue yielded the superscribed substance. Boiling point 130° C.–132° C. at a pressure of 0.1 mm.

(7) [(α-methyl-4-chlorobenzylidene amino)oxy]-N-methyl acetamide.

A mixture of 5.0 g of the [(α-methyl-4-chlorobenzylidene amino)oxy] acetic acid methyl ester obtained by the method described in example 3 and 40 ml of 35% aqueous methylamine solution was stirred for 2 hours. The precipitated solid substance was then dissolved by thrice extracting the mixture with an ether chloroform mixture. The extract was washed thrice with water, dried over anhydrous sodium sulfate and then concentrated by evaporation. Crystallisation of the residue from a benzene petroleum ether mixture yielded the above substance. Melting point 115° C.–116° C.

(8) [(α-methyl-4-chlorobenzylidene amino)oxy]-N,N-dimethyl acetamide.

The above substance was obtained from 5.0 g of [(α-methyl-chlorobenzylidene amino)oxy] acetic aic methyl ester and 50 ml of 25% aqueous dimethylamine solution by the method described in example 7. Melting point 64.5° C.–68° C.

(9) [(α-methyl-3,4-dichlorobenzylidene amino)oxy] acetamide.

A solution of 5.0 g of 3′, 4′-dichloroacetophenone in 50 ml of 90% ethanol was mixed with 2.4 g of aminooxyacetamide and subsequently boiled. The solvent was removed in a vacuum and the residue was extracted with chloroform. The chloroform solution was washed thrice with water, dried over anhydrous sodium sulfate and subsequently concentrated by evaporation in a vacuum. After the addition of ether and petroleum ether the superscribed substance crystallized out from the concentrate. Melting point 111° C.–111.5° C.

(10) [(α-methyl-4-chlorobenzylidene amino)oxy] acetic acid methyl ester.

Of the (α-methyl-4-chlorobenzylidene amino)oxy acetonitrile (melting point 57° C.–58.5° C.) which was obtained by reacting the sodium salt of 4′-chloroacetophenone oxime, with chloroacetonitrile in dimethylformamide, an amount of 11.3 g was dissolved in diisopropyl ether in which 1.94 g of hydrogen chloride and 1.73 g of methanol had also been dissolved. The solution was diluted with 25 ml of diisopropyl ether and subsequently stirred over night. Then the precipitate was drawn off, washed with absolute ether and dried in a vacuum. The resulting hydrochloride of methyl (α-methyl-4-chlorobenzylidene amino)oxy acetimidate melted at 95° C. with decomposition. After this substance had been dissolved in water, the superscribed ester separated out from the solution. It was extracted with ether and distilled in a vacuum. Boiling point at a pressure of 0.1 mm: 130° C.–132° C.

(11) [(α-methyl-4-chlorobenzylidene amino)oxy] acetic acid.

Of the [(α-methyl-4-clorobenzylidene amino)oxy] acetonitrile described in example 10, 1.0 g was dissolved in 20 ml of 0.5 N alcoholic potassium hydroxide. This solution was allowed to stand at room temperature for 3 days, after which the crystallized substance was drawn off. It was dissolved in 20 ml of water, the solution was acidified with 2 N hydrochloric acid and then extracted with ether. From this ethereal solution the above substance was obtained after evaporation of the solvent. Melting point 115.5° C.–116.5° C.

(12) 3-[(α-methyl-4-chlorobenzylidene amino)oxy] propionic acid.

10.2 g of 4′-chloroacetophenone oxime was added to a solution of 1.38 g of sodium in 75 ml of ethanol. After the oxime had dissolved, the solvent was removed in a vacuum and the residue was suspended in 150 ml of benzene. To this suspension a solution of 4.32 g of β-propiolactone in 20 ml of benzene was added with stirring and cooling to 5° C. in a nitrogen atmosphere. The reaction mixture was then stirred for 1.5 hour at 5° C. and subsequently for 2 hours at room temperature. Thereupon, the solvent was distilled off in a vacuum at 30° C. and the residue was mixed with 750 ml of water. The non-dissolved substance was removed by filtration, after which the solution was acidified with acetic acid and extracted thrice with 150 ml of ether. The ethereal extract was washed thrice with 25 ml of water and then extracted with 2 N sodium hydroxide. The alkaline extract was washed twice with ether, then acidified with 2 N hydrochloric acid and then extracted thrice with 150 ml of ether. The latter ethereal extracts were washed thrice with a small amount of water and then dried over sodium sulfate. After the ether had been distilled off, a solid substance of the superscribed structure was left, which after crystallisation from petroleum ether melted in a range from 80° C. to 83° C.

(13) 3-[(α-methyl-4-chlorobenzylidene amino)oxy] propionic acid.

In 10 minutes 75 g of acrylic acid ethyl ester was added drop by drop with stirring to a solution of 41.4 g of 4′-chloroacetophenone oxime in 75 ml of sodium ethylate solution (made from 0.50 g of sodium and ethanol). After the addition, the mixture was cooled to room temperature, and then stirred for 16 hours. Subsequently, 3.0 ml of acetic acid was added and the resulting mixture was concentrated by evaporation at 70° C. and a pressure of 0.01 mm until no longer anything distilled over. The residue was mixed with 300 l of petroleum ether and the resulting solution was filtered. The filtrate was washed thrice with dilute sodium hydroxide, then dried over anhydrous sodium sulfate, and finally concentrated by evaporation at a temperature of 50° C. and a pressure of 12 mm. The residue consisted of the ethyl ester of the 3[(α-ethyl-4-chlorobenzylidene amino)oxy] propionic acid (boiling point 130° C.–132° C. at a pressure of 0.7 mm). By allowing a 5% solution of this ester in 0.5 N alcoholic potassium hydroxide to stand for 24 hours at room temperature the potassium salt of the above-mentioned acid was obtained. By extracting an aqueous solution of this salt after acidification with an equivalent amount of 2 N hydrochloroic acid with ether, drying the ethereal extract and concentrating it by evaporation, the above-mentioned acid was obtained. Melting point range from 80° C. to 85° C.

(14) 3-[(α-methyl-4-chlorobenzylidene amino)oxy] propionamide.

15.6 g of the ethyl ester of 3[(α-methyl-4-chlorobenzylidene amino)oxy] propionic acid obtained by the method described in Example 13 was dissolved in 100 ml of methanol saturated with ammonia at 25° C. This solution was heated at 70° C. in an autoclave for 7 hours. It was then concentrated by evaporation in a vacuum at 40° C. and the semisolid residue was dissolved by means of 200 ml of diethyl ether, 100 ml of benzene, 200 ml of chloroform and 200 ml of methylene chloride. The resulting solution was extracted thrice with dilute sodium hydroxide, then dried over anhydrous sodium sulfate and finally concentrated by evaporation in a vacuum. The residue obtained was recrystallized from a mixture of 50 ml of benzene, 50 ml of chloroform and 25 ml of petroleum ether. Melting point 149° C.–150° C.

(15) 3-[(α-methyl-4-chlorobenzylidene amino)oxy] propionic acid.

A solution of 2.4 g of sodium hydroxide in 55 ml of 85% ethanol was mixed with 6,78 g of 4'-chloroacetophenone oxime and 2.88 g of acrylic acid. The mixture was then refluxed for 2.5 hours, subsequently diluted with 10 ml of water, and concentrated by evaporation in a vacuum after 2 hours. The residue was dissolved in 50 ml of ether and 50 ml of water, and the layers were separated. The water layer was extracted with 50 ml of ether and then acidified with 40 ml of 2 N hydrochloric acid. The acid solution was extracted with 100 ml of ether and the ethereal solution was dried over sodium sulfate. Then the solvent was distilled off and its last traces were removed together with higher boiling substances at a pressure of 0.01 mm and a temperature of 50° C. The residue was crystallized from petroleum ether. Melting point 80° C.-83° C.

(16) 4-[(α-methyl-4-chlorobenzylidene amino)oxy] butyric acid.

A solution of 11.9 g of 4'-chloroacetophenone oxime in 28 ml of N-methyl-2-pyrrolidon was mixed with 1.72 g of comminuted sodium and stirred at 60° C. until all the sodium had dissolved. The reaction mixture was then cooled to room temperature and subsequently mixed with 6.0 g of j-butyrolactone. The reaction mixture was then heated to boiling and refluxed for 4 hours. After part of the solvent had been distilled off in vacuum, the residue was poured into 1 liter of water. The aqueous solution was filtered and then acidified with acetic acid. As a result, a substance having the superscribed structure separated out. It was drawn off, washed with water and recrystallised from 30% acetic acid. Melting point 106.5° C.-108.5° C.

(17) [(α-methyl-4-chlorobenzylidene amino)oxy] acet hydrazide.

A mixture of 5.0 g of the substance obtained by the method of Example 10 and 10 ml of hydrazine hydrate was stirred at room temperature for half an hour. The excess of hydrazine was distilled off in a vacuum and the residue was mixed with water and chloroform. After the chloroform layer had been separated off, the water layer was twice extracted with chloroform. The collected chloroform solutions were washed with water and dried over sodium sulfate. The solution was concentrated by evaporation, the residue was absorbed in a mixture of chloroform, diethyl ether and petroleum ether. A crystalline substance having a melting point at 119° C.-120° C. was obtained.

The following substances were prepared by methods similar to those described in the above examples.

(18) A tablet containing 0.2 g of [(α-methyl-4-chlorobenzylidene amino)oxy] acetic acid.

200 g of [(α-methyl-4-chlorobenzylidene amino)oxy] acetic acid was mixed with 190 g of sec. calcium phosphate, 90 g of microcrystalline cellulose and 120 g of a mixture consisting of 200 parts of maize starch, 32 parts of talcum and 4 parts of magnesium stearate, until a homogeneous mixture had been obtained. From this mixture tablets having a diameter of 13 mm and a weight of 600 mg each were struck.

(19) A suppository containing 0.1 g of [(α-methyl-4-chlorobenzylidene amino)oxy] acetamide.

100 mg of [(α-methyl-4-chlorobenzylidene amino)oxy] acetamide together with 1.5 g of suppository medium was shaped to form a suppository.

(20) Injection liquid.

100 g of [(α-methyl-4-chlorobenzylidene amino)oxy] acetic acid was dissolved in an equimolar amount of 1 N sodium hydroxide, and the solution was mixed with 15 g of benzyl alcohol. This solution was diluted with distilled water to a volume of 1000 mg. The dilute solution was filtered through a bacterial filter, after which ampoules of 1 or 2 ml are aseptically filled with it.

What we claim is:

1. [(a-methyl-4-chlorobenzylidene amino)oxy] acethydrazide.

2. An anti-inflammatory composition comprising as an active ingredient a compound of the formula:

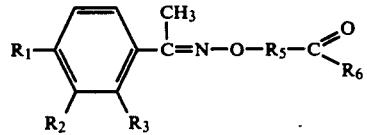

wherein
$R_1$ is a member selected from the group consisting of halogen, $CF_3$, $CH_3$, $SO_2CH_3$, $SO_2NH_2$ and hydrogen,
$R_2$ is a member selected from the group consisting of halogen, methyl and hydrogen with the proviso that $R_2$ is hydrogen only when $R_1$ is other than hydrogen,
$R_3$ is a member selected from the group consisting of hydrogen and halogen, with the proviso that $R_3$ is only halogen when $R_2$ is hydrogen,
$R_5$ is alkylene of up to 3 carbon atoms, $R_6$ is a member selected from the group consisting of OH, alkoxy of up to 8 carbon atoms, $NHNH_2$, $NH_2$, monoalkylamino of up to 3 carbon atoms, dialkylamino of Table

| $R_1$ | $R_2$ | $R_3$ | $R_4$ | $R_5$ | $R_6$ | phys. const. °C. | corresponding example |
|---|---|---|---|---|---|---|---|
| F | H | H | $CH_3$ | $CH_2$ | OH | 104–105.5 | 2 |
| Cl | H | H | $CH_3$ | $CH_2$ | $OCH(CH_3)_2$ | bp 0.7 mm 130–132 | 6 |
| H | Cl | H | $CH_3$ | $CH_2$ | OH | 93–94.5 | 2 |
| Br | H | H | $CH_3$ | $CH_2$ | OH | 131–133 | 2 |
| $CH_3$ | H | H | $CH_3$ | $CH_2$ | OH | 115–116 | 2 |
| $CH_3SO_2$ | H | H | $CH_3$ | $CH_2$ | OH | 144–146 mm 173 | 2 |
| Cl | H | H | $CH_3$ | $CH_2$ | $OnC_8H_{17}$ | bp 0.05 mm 173 | 6 |
| Cl | H | H | $CH_3$ | $CH_2$ | $OCH_2C_6H_5$ | bp 0.05 mm 175–195 | 6 |
| Cl | H | Cl | $CH_3$ | $CH_2$ | OH | 87–88 | 2 | up to 3 carbon atoms in each alkyl, benzyl oxy and the group consisting of the radical $OR_7$, where $R_7$ is a member selected from a metal atom, ammonium, hydroxy ethyl dimethyl ammonium and hydroxy ethyl diethyl ammonium in an anti-inflammatory effective amount and a finely divided pharmaceutical carrier therefor.

3. The anti-inflammatory composition of claim 2 wherein the active ingredient is a compound of the formula

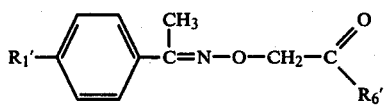

wherein $R_1'$ is a member selected from the group consisting of chlorine and bromine and $R_6'$ is a member selected from the group consisting of $NH_2$, OH, an alkoxy group of up to three carbon atoms and the radical $OR_7$, where $R_7$ has the same meaning as in the formula of claim 1.

4. The anti-inflammatory composition of claim 2 wherein the active ingredient is a compound of the formula

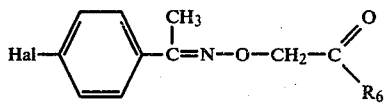

wherein Hal is a halogen selected from the group consisting of Cl and Br and $R_6$ is a moiety selected from the group consisting of OH, $NH_2$, $OCH_3$ and $OR_7$ wherein $R_7$ is a member selected from the group consisting of ammonium, hydroxy ethyl dimethyl ammonium, hydroxy ethyl diethyl ammonium and a metal ion selected from the group consisting of Na, Ca, Mg, Zn and K.

5. The anti-inflammatory composition of claim 3 wherein the active ingredient is [(α-methyl-4-bromobenzylidene amino)oxy] acetic acid and its salts.

6. The anti-inflammatory composition of claim 3 wherein the active ingredient is [(α-methyl-4-chlorobenzylidene amino)oxy] acetic acid and its salts.

7. The anti-inflammatory composition of claim 3 wherein the active ingredient is [(α-methyl-4-bromobenzylidene amino)oxy] acetic acid methyl ester.

8. The anti-inflammatory composition of claim 3 wherein the active ingredient is [(α-methyl-4-bromobenzylidene amino)oxy] acetamide.

9. A method of alleviating inflammatory symptoms in a patient suffering therefrom, comprising administering to said patient a anti-inflammatory composition of claim 2 in a therapeutically effective amount.

10. The method of claim 9 wherein the composition is orally administered.

11. The method of claim 9 wherein the composition is parenterally administered.

* * * * *

UNITED STATES PATENT OFFICE
CERTIFICATE OF CORRECTION

Patent No. 4,196,216    Dated April 1, 1980

Inventor(s) JAN VAN DIJK et al

It is certified that error appears in the above-identified patent and that said Letters Patent are hereby corrected as shown below:

On Title Page, under item [73], change Assignee from " U.S. Philips Corporation, New York, N.Y. "

to -- Duphar International Research B.V. --

Signed and Sealed this

Ninth Day of June 1981

[SEAL]

*Attest:*

RENE D. TEGTMEYER

*Attesting Officer*    *Acting Commissioner of Patents and Trademarks*